United States Patent [19]

Yannas et al.

[11] 4,280,954
[45] Jul. 28, 1981

[54] CROSSLINKED COLLAGEN-MUCOPOLYSACCHARIDE COMPOSITE MATERIALS

[75] Inventors: Ioannis V. Yannas, Newtown Center; Philip L. Gordon, Lexington, both of Mass.; Chor Huang, Avon Lake, Ohio; Frederick H. Silver, Danville, N.H.; John F. Burke, Belmont, Mass.

[73] Assignee: Massachusetts Institute of Technology, Cambridge, Mass.

[21] Appl. No.: 30,183

[22] Filed: Apr. 16, 1979

Related U.S. Application Data

[63] Continuation of Ser. No. 890,427, Mar. 27, 1978, abandoned, which is a continuation-in-part of Ser. No. 596,111, Jul. 15, 1975, abandoned.

[51] Int. Cl.$^3$ ............................................. A23J 1/10
[52] U.S. Cl. ............................. 260/123.7; 128/335.5
[58] Field of Search ................... 260/123.7; 128/335.5

[56] References Cited

U.S. PATENT DOCUMENTS 3,189,401  6/1965  Griset ................................ 128/335.5
3,527,225  9/1970  Smith ................................ 260/123.7

FOREIGN PATENT DOCUMENTS 7325701  2/1975  France .
 472219  5/1969  Switzerland .

OTHER PUBLICATIONS

Chemical Abstracts, vol. 81, No. 116031n, Gelman, 1974.

*Primary Examiner*—Paul R. Michl
*Attorney, Agent, or Firm*—Arthur A. Smith, Jr.; David E. Brook

[57] ABSTRACT

Composite materials are disclosed which are formed by contacting collagen with a mucopolysaccharide and subsequently covalently crosslinking the resultant polymer. These composite materials have a balance of mechanical, chemical and physiological properties which make them useful in surgical sutures and prostheses of controlled biodegradability (resorption) and controlled ability to prevent development of a foreign body reaction, and many are also useful in applications in which blood compatibility is required.

11 Claims, No Drawings

CROSSLINKED COLLAGEN-MUCOPOLYSACCHARIDE COMPOSITE MATERIALS

GOVERNMENT SUPPORT

Research described herein was supported by the U.S. Department of Health, Education and Welfare, National Institutes of Health.

RELATED APPLICATIONS

This a continuation of application Ser. No. 890,427 filed Mar. 27, 1978, now abandoned which is a continuation-in-part of Ser. No. 596,111, filed July 15, 1975, now abandoned.

BACKGROUND OF THE INVENTION

1. Field of the Invention

The invention is in the field of materials and more particularly in the field of composite polymeric materials having suitable properties for medical and surgical applications.

2. Description of the Prior Art

Collagen, a major protein constituent of connective tissue in vertebrate and invertebrate animals, is widely used in medical and surgical applications in the fabrication of surgical sutures, blood vessel grafts, and in all forms of surgical prostheses. While collagen is better than most materials for such applications, it does have some significant deleterious properties.

One such property is the low resistance of collagen to resorption since it is a resorbable animal protein which is degraded by tissue enzymes (collagenases) present at implantation sites. Attempts have been made to solve this problem by crosslinking collagen, but these attempts have turned out to be only partially successful because rather high degrees of crosslinking are required to make collagen non-resorbable. Although crosslinking solves one problem, it creates another—that is, the tensile strength and other mechanical properties of collagen can suffer significantly when an excessively large degree of crosslinking is required to control the resorption to a very low level.

Other researchers have modified the properties of collagen by reacting it with other materials. Smith, in U.S. Pat. No. 3,527,225, describes resorbable surgical sutures formed from protein fibrils, such as collagen fibrils, which are oriented and crosslinked with up to 6% of polybasic polyacids, such as mucopolysaccharide acids. Smith also discloses that a very light treatment with formaldehyde or a very light chrome tanning improves the knot holding capability of these sutures without largely increasing resorption time.

Another deleterious property exhibited by collagen, insofar as its uses in surgical prostheses and other such applications are concerned, is that collagen, like most other polymeric materials, is non-compatible with blood. To qualify as blood-compatible, a material must not cause either platelet aggregation (white thrombus) or clotting of red cells (blood clot). Collagen causes both. Blood platelets are known to adhere to exposed collagen, such as occurs when blood vessels are mechanically injured, and this collagen-platelet interaction causes platelet aggregation. The detailed mechanistic aspects of this interaction have been extensively studied and reported in the literature. See, for example: Muggli, R. and Baumgartner, H. R., *Thromb. Res.*, 3, 715 (1973); and Michaeli, D. and Orloff, K. G., *Progress in Hemostasis and Thrombosis*, T. H. Spaet, Ed., Gune and Stratton, N.Y., 3, 29 (1976). In addition, collagen has been implicated in acceleration of blood clotting by activation of Hageman factor (clotting factor XII). See Wilner, C. D., Nossel, H. L. and LeRoy, E. C., *J. Clin. Invest.*, 47, 2608 (1968).

Previous efforts to synthesize blood compatible materials have centered largely around attempts to attach a blood-compatible material to the surface of a non-compatible material. The most successful materials were formed by attaching heparin, a known anticoagulant, to the surface of various synthetic polymers.

Attachment of heparin to such surfaces has been achieved by a variety of techniques, which are generally classifiable as either ionic interaction or chemical reaction. Both of these general techniques suffer from disadvantages, however. If the substrate surface is not completely covered, the uncovered portions which contact blood can cause formation of a thrombus or clot. Additionally, the possibility exists that, during the handling or use of such covered materials, the surface coating of heparin can become detached due to a mechanical incident or become hydrolyzed or otherwise be attacked chemically or biochemically by substances found in the blood or in vascular tissue; the resulting disruption of the surface coating is followed by exposure of underlying non-compatible substrate. Equally serious perhaps, is the difficulty that heparin occasionally desorbs from the substrate and migrates into the blood where, by virtue of its being a potent anticoagulant, heparin interferes strongly with the competence of healthy blood to clot, which is generally undesirable.

SUMMARY OF THE INVENTION

This invention relates to the synthesis of new composite materials suitable for a wide variety of medical and surgical uses. Such materials are formed by intimately contacting collagen with a mucopolysaccharide under conditions at which they form a reaction product and subsequently covalently crosslinking the reaction product. Suitable collagen can be derived from a number of animal sources, either in the form of a solution or in the form of a dispersion, and suitable mucopolysaccharides include, but are not limited to chondroitin 4-sulfate, chondroitin 6-sulfate, heparan sulfate, dermatan sulfate, keratan sulfate, heparin and hyaluronic acid.

Covalent crosslinking can be achieved by chemical, radiation, dehydrothermal or other covalent crosslinking techniques. A suitable chemical technique is aldehyde crosslinking, but other chemical crosslinking reactants are equally suitable. Dehydrothermal crosslinking, which is preferred, is achieved by reducing the moisture level of the composites to a very low level, such as by subjecting the composite material to elevated temperatures and high vacuum. Dehydrothermal crosslinking eliminates the necessity to add, and in the case of toxic materials such as aldehydes, to remove unreacted crosslinking agents; dehydrothermal crosslinking also produces composite materials containing a wider range of mucopolysaccharide content than is achieved with some chemical crosslinking techniques.

The products of such syntheses are collagen molecules or collagen fibrils with long mucopolysaccharide chains attached to them. Covalent crosslinking anchors the mucopolysaccharide chains to the collagen so that a significant residual quantity of mucopolysaccharide remains permanently bound to collagen even after washing in strong mucopolysaccharide solvents for several weeks. Mechanically, these materials can be thought of as analogous to fiber reinforced composite materials wherein collagen is the fiber and mucopolysaccharide is the matrix; therefore, these materials are sometimes referred to herein as composite polymeric materials.

Covalently crosslinked collagen-mucopolysaccharide composites have been found to retain the advantageous properties of native collagen. Unexpectedly, however, it has been found that these materials, even when they are relatively highly crosslinked, have outstanding mechanical properties. Such materials can be synthesized, for example, which have ultimate tensile strength, elongation at break, and other mechanical properties equal to or higher than collagen crosslinked to the same level of the crosslink density. In many cases, the mechanical properties of crosslinked collagen-mucopolysaccharide composite materials exceed those of native collagen which is not artificially crosslinked. Because of this, the collagen-mucopolysaccharide composites can be crosslinked to provide any desired degree of increased resistance to resorption over the low degree exhibited by native collagen which is not artificially crosslinked. In fact, the crosslinking can provide essentially complete resistance, if desired. The ability to tailor the degree of resistance to resorption without sacrificing mechanical properties provides a degree of design flexibility for surgical prostheses, etc., heretofore unavailable with any class of resorbable materials.

Surprisingly, many of the crosslinked collagen-mucopolysaccharide composites described herein have been found to be compatible with blood. One such material can be formed from collagen, a known thrombogenic material, and chondroitin 6-sulfate. Chondroitin 6-sulfate is as soluble in blood as heparin is but, unlike heparin, it has such a low level of anticoagulant activity that it can be considered to be inert in this regard. (Tests show, for example, that chondroitin 6-sulfate has between 1/3000 and 1/5000 the anticoagulant activity of heparin at equivalent concentrations). Reaction with mucopolysaccharides appears to suppress essentially the entire procoagulant activity and thrombogenic nature of native collagen. Thus, many of these composites do not cause blood platelet aggregation, do not cause clotting, and, with the exception, under certain conditions, of the collagen-heparin composites, do not interfere with the competence of blood to clot. Since the materials are homogeneous, all problems associated with surface coverage of thrombogenic materials with blood-compatible materials are obviated.

DESCRIPTION OF PREFERRED EMBODIMENTS

Collagen is a major protein constituent of connective tissues in vertebrate as well as invertebrate animals. It is often present in the form of macroscopic fibers which can be chemically and mechanically separated from non-collagenous tissue components. Collagen derived from any source is suitable for use with this invention, including insoluble collagen, collagen soluble in acid, in neutral or basic aqueous solutions, as well as those collagens which are commercially available. Typical animal sources include calfskin, bovine Achilles tendon, cattle bones and rat tail tendon.

Several levels of structural organization exist in collagen. The primary structure consists of the complete sequence of amino acids. Collagen is made up of 18 amino acids in relative amounts which are well known for several animal species but in sequences which are still not completely determined. The total content of acidic, basic and hydroxylated amino acid residues far exceeds the content of lipophilic residues making collagen a hydrophilic protein. Because of this, polar solvents with high solubility parameters are good solvents for collagen.

At least two sets of characteristics which differentiate collagen from other proteins are: (1) the amino acid composition which is not only unique but is also distinctive because of its high content of glycyl, prolyl and hydroxyprolyl residues; and (2) the wide-angle x-ray diffraction pattern which shows a strong meridional arc corresponding to a spacing of about 2.9 A and a strong equatorial spot corresponding in moist collagen to a spacing of about 15 A. A more detailed physicochemical definition of collagen in the solid state is given in Yannas, I. V., "Collagen and Gelatin in the Solid State", *J. Macromol. Sci.—Revs. Macromol. Chem.*, C7(1) 49–104 (1972).

The term mucopolysaccharide describes hexosamine-containing polysaccharides of animal origin. Another name often used for this class of compounds is glycosaminoglycans. Chemically, mucopolysaccharides are alternating copolymers made up of residues of hexosamine glycosidically bound and alternating in a more-or-less regular manner with either hexuronic acid or hexose moieties. See Dodgson, K. S., and Lloyd, A. G., in *Carbohydrate Metabolism and its Disorders*, ed. by F. Dickens, et al., vol. 1, Academic Press (1968).

Some of the better known mucopolysaccharides derived from animals can be represented by the following structural formulas or chemical repeat units:

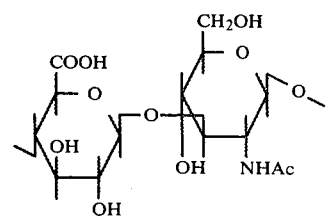

HYALURONIC ACID

-continued

CHONDROITIN 4-SULFATE
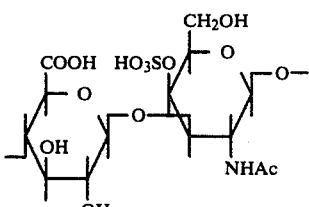

CHONDROITIN 6-SULFATE
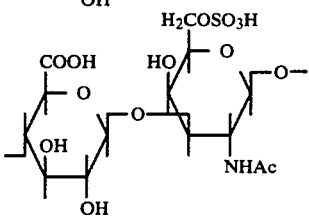

DERMATAN SULFATE
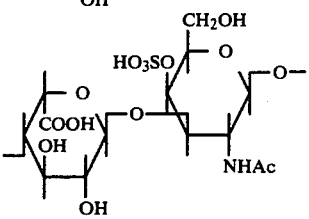

KERATAN SULFATE
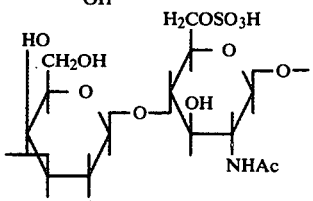

HEPARIN
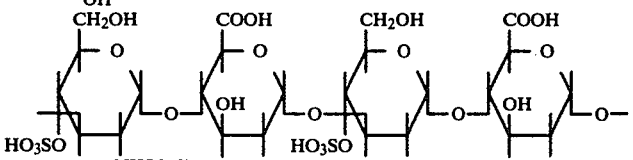

HEPARAN SULFATE
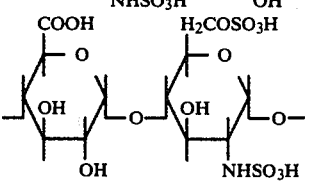

Other mucopolysaccharides are suitable for forming the composite materials described herein, and those skilled in the art will either know or be able to ascertain, using no more than routine experimentation, other suitable mucopolysaccharides. For a more detailed description of mucopolysaccharides, see the following reference, the teachings of which are hereby incorporated by reference: Aspinall, G. O., *Polysaccharides*, Pergamon Press, Oxford (1970).

Typical sources of heparin include hog intestine, beef lung, borine liver capsule and mouse skin. Hyaluronic acid can be derived from rooster comb and human umbilical cord, whereas both chondroitin 4-sulfate and chondroitin 6-sulfate can be derived from bovine cartilage and shark cartilage. Dermatan sulfate and heparan sulfate can be derived from hog mucosal tissues while keratan sulfate can be derived from the bovine cornea.

Collagen can be reacted with a mucopolysaccharide in aqueous acidic solutions. These reactions can be carried out at room temperature. Typically, small amounts of collagen, such as 0.3% by weight, are dispersed in a dilute acetic acid solution and thoroughly agitated. The polysaccharide is then slowly added, for example dropwise, into the aqueous collagen dispersion, which causes the coprecipitation of collagen and mucopolysaccharide. The coprecipitate is a tangled mass of collagen fibrils coated with mucopolysaccharide which somewhat resembles a tangled ball of yarn. This tangled mass of fibers can be homogenized to form a homogeneous dispersion of fine fibers and then filtered and dried. Collagen-mucopolysaccharide coprecipitation products have been studied by Podrazky, V., Steven, F. S., Jackson, D. S., Weiss, J. B. and Leibovich, S. J., *Biochim. Biophys. Acta.*, 229, 690 (1971).

Studies were made of the effect of temperature and pH on the reaction between collagen and six mucopolysaccharides, i.e., hyaluronic acid, dermatan sulfate, chondroitin 4-sulfate, chondroitin 6-sulfate, heparin and heparan sulfate. It was found that at both 23° C. and 37° C., the amount of mucopolysaccharide attached to the collagen was small at pH values above about 6. The amount of mucopolysaccharide increased with decreasing pH but appeared to level off at a pH of about 3 for some mucopolysaccharides. At pH values below about 5, the amount of mucopolysaccharide attached at 37° C. was often about 2-3 times that at 23° C. It was also found that materials prepared at 37° C. and a pH considerably less than 3 were partially denatured (gelatinized). Thus, the conditions for maximum attachment of mucopolysaccharide without significant partial denaturation (gelatinization) were found to be a pH of about 3 and a temperature of about 37° C. Although these conditions are preferred, other reaction conditions which result in a significant reaction between collagen and a mucopolysaccharide are also suitable.

At relatively low concentrations of mucopolysaccharide in the original solution, it was found that most of the mucopolysaccharide interacted with the collagen fibers that were precipitated. As the relative concentration of mucopolysaccharide increased, the proportion of interacted mucopolysaccharide decreased.

Although the collagen-mucopolysaccharide reaction product coprecipitates from the aqueous medium from which it is formed it has been found that the mucopolysaccharide component can dissolve in other aqueous solutions. This is particularly true for more concentrated aqueous salt solutions, such as body fluids. It is known, for example, that collagen-mucopolysaccharide coprecipitates are insoluble in 0.01 M NaCl, somewhat soluble in 0.1 M NaCl, and quite soluble in 0.04 M NaCl—the physiological level is about 0.14 M NaCl. Thus, these reaction products have only limited insolubility and are not suitable, per se, as candidate materials for implantable surgical prostheses, etc.

While the coprecipitation method described supra is preferred, collagen and mucopolysaccharides can be reacted in other ways. The essential requirement is that the two materials be intimately contacted under conditions which allow the mucopolysaccharides to attach to the collagen chains. Another suitable technique is to coat collagen with mucopolysaccharide, such as by dipping articles formed from collagen, including sheets, films, and tubes, into a solution of mucopolysaccharide. A suitable variation of the latter technique involves prior coating with collagen of an article, sheet, film or tube fabricated from a non-collagenous material, such as a synthetic, natural or modified natural polymer, followed by dipping of the collagen-coated article, sheet, film or tube into the mucopolysaccharide solution. Still another suitable method is to intimately mix collagen with mucopolysaccharides, with each component in the form of a dry powder.

It will be clear that the collagen-mucopolysaccharide product prepared as described above could be formed into sheets, films, tubes and other shapes or articles for its ultimate application.

To gain any significant increase in resistance to collagen resorption, it is necessary to have at least about 0.5% by weight of mucopolysaccharide bound to the collagen chains. The upper limit may be set by the sites on collagen which are available for mucopolysaccharide attachment. For composites wherein the mucopolysaccharide in chondroitin 6-sulfate, levels of about 28% by weight have been achieved; with hyaluronic acid, on the other hand, the upper limit achieved is about 25%.

Reaction with the mucopolysaccharides also provides collagen with another valuable property, i.e., inability to provoke an immune reaction (foreign body reaction) from an animal host. To convert collagen into a material which, when implanted, would not be recognized as a foreign body requires reacting it with at least about 1% by weight of mucopolysaccharide.

The degree of insolubility of the collagen-mucopolysaccharide products can be raised to the desired degree by covalently crosslinking these materials. In general, any covalent crosslinking method suitable for crosslinking collagen is also suitable for crosslinking these composite materials. Such covalent crosslinking serves to prevent dissolution of mucopolysaccharide in aqueous solutions thereby making the materials useful for surgical prostheses, etc.

Covalent crosslinking also serves another important function by contributing to raising the resistance to resorption of these materials. The exact function of crosslinking is not understood in this regard, but it may be that crosslinking anchors the mucopolysaccharide units to sites on the collagen chain which would normally be attacked by collagenase. Another possible explanation is that crosslinking tightens up the network of collagen fibers and physically restricts the diffusion of enzymes capable of degrading collagen.

It has been found that the crosslinked composites should have an $M_c$ (number average molecular weight between crosslinks) of between about 800 and about 60000. Materials with $M_c$ values below about 800 or above about 60000 suffer significant losses in their mechanical properties. Composites with an $M_c$ of between about 5000 and about 10,000 appear to have the best balance of mechanical properties, and so this is the preferred range of crosslinking for products requiring such a balance of properties.

Covalent crosslinking can be achieved by many specific techniques with the general categories being chemical, radiation and dehydrothermal methods. An advantage to most crosslinking techniques contemplated, including glutaraldehyde crosslinking and dehydrothermal crosslinking, is that they also serve in removing bacterial growths from the materials. Thus, the composites are being sterilized at the same time that they are crosslinked.

One suitable chemical method for covalently crosslinking the Collagen-mucopolysaccharide composites is known as aldehyde crosslinking. In this process, the materials are contacted with aqueous solutions of aldehyde, which serve to crosslink the materials. Suitable aldehydes include formaldehyde, glutaraldehyde and glyoxal. The preferred aldehyde is glutaraldehyde because it yields the desired level of crosslink density more rapidly than other aldehydes and is also capable of increasing the crosslink density to a relatively high level. It has been noted that immersing the composites in aldehyde solutions causes partial removal of the polysaccharide component by dissolution thereby lessening the amount of polysaccharide in the final product. Unreacted aldehydes should be removed from the collagen-mucopolysaccharide materials since residual aldehydes are quite toxic.

Other chemical techniques which are suitable include carbodiimide coupling, azide coupling, and diisocyanate crosslinking.

A preferred crosslinking method is referred to herein as a dehydrothermal process. In dehydrothermal crosslinking, it is not necessary to add external crosslinking agents. The key is to dehydrate the product to be crosslinked to a moisture content of less than about 1%. The amount of water which must be removed will vary with many factors, but, in general, sufficient water to achieve the desired density of crosslinking must be removed. Thus, the collagen-mucopolysaccharide product can be subjected to elevated temperatures and/or vacuum conditions until the moisture content is reduced to extremely low levels. In the absence of vacuum, temperatures above about 80° C., and preferably above 90° C., can be used. At 23° C., vacuum of at least about $10^{-5}$ mm. of mercury, and preferably below $10^{-6}$ mm. of mercury, are suitable. Elevated temperature and vacuum can be also used in combination; this, in fact, is the most expeditious route and is therefore preferred. With a vacuum of at least about $10^{-5}$ mm. of mercury, it is preferred to use a temperature of at least about 35° C. In general, the materials are subjected to the elevated temperatures and vacuum conditions until the degree of insolubility desired is obtained. The higher the temperature, the lower is the vacuum required to arrive at a given crosslink density; and vice versa. A typical crosslinking process to attain an $M_c$ between about 5000 and 10000 would involve subjecting the collagen-mucopolysaccharide material to a temperature of 95° C. and a vacuum of 0.01 mm. of mercury for 24 hours. This dehydrothermal crosslinking process overcomes certain disadvantages of the aldehyde crosslinking method and produces composites having relatively large amounts of mucopolysaccharide strongly bound to the collagen chain.

The exact mechanism operating in the dehydrothermal crosslinking process is not known. However, it may be either an amide condensation involving ε-amino groups from collagen and carboxyl groups from the mucopolysaccharide component, or esterification involving carboxyl groups from collagen and hydroxyl groups from the mucopolysaccharide or esterification involving carboxyl groups from the mucopolysaccharide component and hydroxyl groups from collagen. Possibly all three mechanisms are involved to some extent. For a more detailed description of dehydrothermal crosslinking, see Yannas, I. V. and Tobolsky, A. V., "Crosslinking of Gelatin by Dehydration", Nature, vol. 215, #5100, pp. 509–510, July 29, 1967, the teachings of which are hereby incorporated by reference.

To be suitable for vascular prostheses, materials must have certain minimum mechanical properties. These are mechanical properties which would allow the suturing of candidate materials to sections of natural vessel, a process known as anastomosis. During suturing, such vascular (blood vessel) grafts must not tear as a result of the tensile forces applied to them by the suture nor should they tear when the suture is knotted. Suturability of vascular grafts, i.e., the ability of grafts to resist tearing while being sutured, is related to the thickness of the graft, the tension applied to the suture, and the rate at which the knot is pulled closed. Experimentation performed indicates that the minimum mechanical requirements for suturing a graft of at least 0.01 inches in thickness are: (1) an ultimate tensile strength of at least 50 psi; and, (2) an elongation at break of at least 10%.

The best materials for vascular prostheses should duplicate as closely as possible the mechanical behavior of natural vessels. The most stringent physiological loading conditions occur in the elastic arteries, such as the aorta, where fatigue can occur as a result of blood pressure fluctuations associated with the systole-diastole cycle. The static mechanical properties of the thoracic aorta can be used as a mechanical model. The stress-strain curve of the thoracic aorta in the longitudinal direction of persons 20–29 years of age has been determined by Yamada. See Yamada, H., *Strength of Biological Materials*, ed. F. G. Evans, Chapter 4, Williams & Wilkins (1970). From this plot, the mechanical properties were calculated and found to be: (1) an ultimate tensile strength of 360 psi; (2) elongation at break of 85%; (3) tangent modulus at 1% elongation of 50 psi; and (4) fracture work, i.e., the work to rupture (a measure of toughness), of 21,000 psi-%. These four mechanical properties serve as a quantitative standard for mechanical properties of vascular prostheses.

Values for these mechanical properties were determined for collagen-mucopolysaccharide composites as described herein using an Instron tester. As might be expected, the mechanical properties are strongly dependent on the presence of incorporated mucopolysaccharide, the degree of fibrillar aggregation of the collagen fibrils and the number of crosslinks per unit volume. For collagen composites with fibril size controlled at a fixed level, the mechanical behavior becomes a function of the mucopolysaccharide content and the degree of crosslinking Optimum mechanical properties were obtained for pure collagen materials with $M_c$ equal to about 5000–10000. The degree of crosslinking is, of course, the reciprocal of $M_c$, the average molecular weight between crosslinks. Certain collagen-mucopolysaccharide composites prepared by the dehydrothermal crosslinking process had superior elongation at break, strength, and toughness compared to collagen with similar values of $M_c$. Dehydrothermally crosslinked composites easily passed the minimum suturability requirements and possessed mechanical properties approaching those of the thoracic aorta.

Many of the collagen-mucopolysaccharide composite materials described herein have been found to have outstanding compatibility with blood. This is in contrast to most materials, particularly synthetic polymers, which have been found to be almost universally non-compatible with blood. As used herein, "blood-compatible" means that a material compares favorably with human blood vessels in three regards: (1) tendency not to cause platelet aggregation; (2) tendency not to cause clotting of red blood cells; and preferably, (3) tendency not to interfere with the competence of healthy blood to clot.

Both in vitro and in vivo testing has established that many of the collagen-mucopolysaccharide composite materials can be synthesized to be blood-compatible. For example, composites containing either chondroitin 6-sulfate or heparin have been prepared which have whole blood clotting times (WBCT) exceeding sixty minutes, which values are comparable to normal endothelium. The WBCT test is a well-known in vitro procedure for qualitatively evaluating the affect of materials on (1) blood coagulation, (2) platelet aggregation; (3) red blood cell aggregation, and this test is described in more detail in the Examples herein. Other in vitro tests, including the thrombin time (TT), activated partial thrombin time (APTT), prothrombin time (PT), and platelet aggregation tests, as well as in vivo testing, corroborate the blood-compatible nature of many of the materials described herein.

It does appear from the testing done that a certain minimum amount of mucopolysaccharide must react with collagen to achieve blood compatibility. This minimum amount is believed to be about 0.5% by weight based upon the total weight of the composite to produce materials having blood-compatibility significantly better than native collagen. Additionally, the presence of one or more sulfate groups on the chemical repeat unit of the mucopolysaccharide appears to be important, as evidenced by the low WBCT values for composites formed from hyaluronic acid, to provide a material with non-clotting characteristics. Nevertheless, hyaluronic acid composites have not been found to cause platelet aggregation.

Based upon resistance to resorption, freedom from foreign body reaction, mechanical properties and blood-compatibility, crosslinked composites should contain at least about 0.5% bound mucopolysaccharide. Those composites containing between about 6% and about 15% of a sulfate-containing mucopolysaccharide are particularly preferred because of their outstanding properties, including blood-compatibility. The percentage of mucopolysaccharide specified herein is that obtained when the measurement is made immediately after crosslinking. With thorough washing, any mucopolysaccharide which is not covalently bound can be removed.

The crosslinked collagen-mucopolysaccharide composite materials described herein have outstanding properties for many utilities. Primarily, they are useful in medical and surgical applications, specifically for surgical sutures, blood vessel grafts, catheters and in general, the fabrication of surgical prostheses. Additionally, they are useful in the fabrication of artificial organs which pump blood such as artificial kidneys and in the fabrication of blood compatible equipment such as blood oxygenators as well as in the fabrication of miscellaneous equipment for the handling and storage of blood such as pumps, tubes and storage bags.

Materials other than collagen could probably be contacted with chondroitin 6-sulfate and other mucopolysaccharides to yield blood-compatible materials. Such materials could include synthetic polymers such as the segmented polyurethanes, polyhydroxyethyl methacrylate and other "hydrogels", silicones, polyethylene terephthalate and polytetrafluoroethylene or modified natural polymers such as cellulose acetate or natural polymers such as elastin (the fibrous, insoluble, non-collagenous protein found in connective tissues such as the thoracic aorta and ligamentum nuchae) or pyrolytic carbon and other carbons which may have been treated thermally or by an electric arc. Such composites could be formed either by intimate mixing of the powdered solids or mixing of compatible solutions or dispersions of the two components or by coating with a mucopolysaccharide one of the materials mentioned in this paragraph. Irrespective of the method used to contact the mucopolysaccharide with the other material, the two components could be covalently bonded to form a material from which the mucopolysaccharide cannot be dissolved or extracted by contact with mucopolysaccharide solvents such as aqueous electrolytic solutions. Covalent bonding could be effected by a radiation grafting copolymerization technique using, for example, $\gamma$-radiation from a cobalt-60 source. In all such procedures, chondroitin 6-sulfate or other mucopolysaccharides which do not interfere with normal blood clotting if accidentally eluted out of the composite material during use are clearly preferred over heparin which strongly interferes with normal blood clotting.

It is also quite probable that blood-compatible materials could be prepared by bonding, using an adhesive, the crosslinked collagen-mucopolysaccharide composite in the form of a sheet, film, granulated solid or powder or other form onto a variety of substrates. Such substrates would include synthetic polymers such as the segmented polyurethanes, polyhydroxyethyl methacrylate and other "hydrogels", silicones, polyethylene terephthalate and polytetrafluoroethylene or modified natural polymers such as cellulose acetate or natural polymers such as elastin or pyrolytic carbon and other carbons which may have been treated thermally or by an electric arc or metals such as vitalium, titanium and various steels. A suitable adhesive would, for example, be a silicone rubber adhesive.

The invention is further and more specifically illustrated by the following Examples.

EXAMPLE 1

PREPARATION OF COLLAGEN DISPERSIONS AND MUCOPOLYSACCHARIDE SOLUTIONS

The collagen used was prepared by precutting limed calf hides into strips $\frac{3}{8}''$ wide and then into thin pieces. These thin pieces of hide were contacted with three parts of water containing 0.3% propionic acid and 0.1% benzoic acid. Equilibrium was established after four hours at which time the solution had a pH approaching 5.3. The collagen slurry was separated from the water and ground to products of different particle sizes and structures with a centrifugally acting cutter-grinder. The calf hide collagen slurry (1:1 water-to-hide weight ratio) had a gelatin content of about 2%. Additionally, it contained about 0.41% calcium and about 0.041% magnesium. Physically, the slurry was composed of highly entangled fibrillar aggregates.

The calf hide collagen slurry as purified by a repeated precipitation from a turbid dispersion in 0.05 M acetic acid with 0.2$M$ sodium dihydrogen diphosphate, $NaH_2PO_4$. After purification, collagen was dispersed in 0.05 M acetic acid or in a citric acid-buffer solution at pH 3.2 (0.1 M citric acid, 0.2 M sodium dihydrogen diphosphate). The dispersion was thoroughly homogenized in a Waring Blender until the absorbance at 440 millimicrons of a 0.3% (W/V) collagen dispersion was about 0.5 as measured on a spectrophotometer (Coleman Junior II A, Maywood, Illinois). The resulting collagen dispersions were stored at 4° C. until further processing was required.

Mucopolysaccharide solutions were prepared from sodium heparin, hyaluronic acid and chondroitin 6-sulfate. Sodium heparin, from hog intestinal mucosa, 143 U.S.P. units of activity per milligram, was purchased from Abbott Laboratories, North Chicago, Illinois. Hyaluronic acid, from rooster comb was prepared by the method of Swann, D. A., *Biochim. Biophys. Acta,* 156, 17 (1968). The resulting hyaluronic acid contained 47.1% hexuronic acid and 42.6% hexosamine.

Chondroitin 4-sulfate from bovine nasal cartilage was prepared by the method described by Roden, L., Baker, J. R., Cifonelli, J. A. and Mathews, M. B., in *Methods of Enzymology,* V. Ginsburg, ed., vol. 28B, Academic Press, New York, p. 73. Heparan sulfate and dermatan sulfate were both extracted from hog mucosal tissues and purified by the methods described by Cifonelli, J. A. and Roden, L., *Biochemical Preparations,* 12, 12 (1968).

Chondroitin 6-sulfate, from shark cartilage - Grade B, was purchased from Calbiochem, San Diego, Calif. It contained 2.66% nitrogen, 37.2% glucuronic acid and 5.61% moisture.

Heparin, hyaluronic acid, chondroitin 4-sulfate, heparan sulfate, dermatan sulfate and chondroitin 6-sulfate were dissolved (1% W/V) in a citric acid-phosphate buffer pH 3.2. The mucopolysaccharide solutions were stored at 4° C.

EXAMPLE 2

PREPARATION OF COLLAGEN-HEPARIN AND COLLAGEN-HYALURONIC ACID COPRECIPITATES

Collagen 0.3% (W/V) dispersed in 0.05 M acetic acid was thoroughly agitated with a Teflon stirrer at 23° C. While the dispersion was mixing, heparin or hyaluronic acid 1% (W/V) in 0.05 M acetic acid was added drop wise from a buret at the rate of about 0.1 ml. per second. The addition of mucopolysaccharide caused collagen to coprecipitate forming a tangled mass of collagen fibrils coated with mucopolysaccharide which somewhat resembled a tangled ball of yarn. When 90% by weight of collagen was coprecipitated in this manner with 10% by weight mucopolysaccharide, a systematic mass balance showed that about 95% of the added mucopolysaccharide was coprecipitated.

After coprecipitation, the tangled mass of fibrils was homogenized in a Waring Blender until the fibrils were about 1 mm. in length. The mixture of fibrils in 0.05 M acetic acid separated into two phases when left unagitated for more than five minutes, so that mixing was required before filtration. Filtration was performed by filtering the collagen-mucopolysaccharide dispersion under vacuum through a Buchner funnel containing Schleicher and Schuell (Keene, New Hampshire) filter paper No. 576. The coprecipitate was allowed to dehydrate under atmospheric conditions until the moisture content was about 20% by weight.

EXAMPLE 3

PREPARATION OF COLLAGEN-CHONDROITIN 6-SULFATE COPRECIPITATES

Collagen 0.3% (W/V) dispersed in a citric acid-phosphate buffer solution pH 3.2 at 23° C. was coprecipitated with a 1% (W/V) chondroitin 6-sulfate buffer solution pH 3.2 at 23° C. The coprecipitate was homogenized, filtered and allowed to dry in the atmosphere as described in Example 2.

If it is desirable to maintain high porosity in the product, as is often the case with synthetic skin, the composites can be freeze dried. Typical conditions are a temperature of −50° C. and a vacuum of 0.06 mmHg.

EXAMPLE 4

ALDEHYDE CROSSLINKING OF A COLLAGENCHONDROITIN 6-SULFATE COMPOSITE

Coprecipitated collagen-chondroitin 6-sulfate as prepared in Example 3 was covalently crosslinked by immersing it in a 0.02 M solution of glutaraldehyde. This treatment effectively immobilized a fraction of the polysaccharide component on the collagen fibrils or molecules. Crosslinking was evidenced by the inability to remove the polysaccharide from the aldehyde-treated film by prolonged washing with a phosphate buffer solution containing 0.4 M sodium chloride, pH 7.4, which is a well known solvent of chondroitin 6-sulfate. Unreacted aldehydes were removed by treatment with a solution of 5,5-dimethyl-1,3-cyclohexane dione (dimedone). Evaporation of the water left behind a film containing up to about 10% by weight polysaccharide.

EXAMPLE 5

DEHYDROTHERMAL CROSSLINKING OF COLLAGEN-CHONDROITIN 6-SULFATE

The product of Example 3 was placed in a vacuum oven and exposed to a temperature of 115° C. and a vacuum of at least 0.3 mm. Hg. for 48 hours. At the end of this treatment, less than 10 weight percent of the polysaccharide originally incorporated into the film could be removed by 48-hour immersion in distilled water, a solvent for chondroitin 6-sulfate.

EXAMPLE 6

HEXOSAMINE ANALYSIS AND MOLECULAR WEIGHT BETWEEN CROSSLINKS

Since mucopolysaccharides are hexosamine-containing polymers, the level of hexosamine is directly related to the amount of a specific mucopolysaccharide in a composite material. Once a relationship is established between the hexosamine content and weight for each individual mucopolysaccharide, the determination is straightforward. This analysis is described in detail by Huang, C., Sc. D. Thesis, Mech. Eng. Dept., M.I.T., Cambridge, Mass., Chaps. 3, 4 (1974). The method is summarized as follows. A known weight of a vacuum dried (48 hours at 105° C.) composite is placed in a 5 ml. ampule and 1 ml. of 8 M HCl is added. The ampule is evacuated and flushed with nitrogen gas followed by sealing under vacuum. Hydrolysis is initiated when the ampule is placed in a circulating air oven at 95° C. After 4 hours at 95° C., the ampule is cooled with tap water to 10° C. The contents of the tube are then evaporated to dryness at 40° C. until only the dry hydrolyzate remains. The hydrolyzate is dissolved in distilled water to give a concentration of about 50–150 mg. of mucopolysaccharide per ml. of water. One ml. of the hydrolyzate solution is added to 1 ml. of an 8% (V/V) solution of acetylacetone in 1 M Na$_2$CO$_3$. After heating at 95° C. for 1 hour, hexosamine contained in the hydrolyzate reacts with acetylacetone in alkaline solution to form derivatives of pyrrole. Upon cooling the solution to 10° C., 5 ml. of 95% ethanol and 1 ml. of Ehrlich reagent (prepared by dissolving 1.33 g. of p-dimethylamino-benzaldehyde, DAB, in 50 ml. of 6 M HCl to which 50 ml. of 95% ethanol is added) are added followed by thorough mixing. The reaction between DAB and derivatives of pyrrole results in the formation of a chromophore which colors the product an intense red. After the mixture is allowed to stand for 2 hours, the absorbance is measured at 527 nanometers against a reagent blank using a Coleman Junior II A spectrophotometer. The results of the analysis are compared to standard calibration curves for each mucopolysaccharide.

The results of hexosamine analysis on several crosslinked collagen-mucopolysaccharide materials prepared by the methods of previous Examples are presented in Table I. The mucopolysaccharide content before crosslinking was determined to be about 10% for each composite listed in Table 1. It appears that during glutaraldehyde crosslinking and subsequent washing steps, large quantities of mucopolysaccharide were lost. This implies that the solubility of uncrosslinked mucopolysaccharides is high in the aqueous glutaraldehyde solution in which the former are immersed for the purpose of crosslinking them. For the dehydrothermally crosslinked composites, only 10%, at most, of a mucopolysaccharide was eluted, versus up to 61% for the glutaraldehyde process.

The mechanical properties of the composite materials is strongly influenced by the number of crosslinks per polymer chain. The molecular weight between crosslinks ($M_c$) is inversely proportional to the number of crosslinks per unit volume. By measuring the stress-strain behavior of thermally denatured collagen-mucopolysaccharide composites, values of $M_c$ can be determined. The technique is described by Treloar, L. R. G., *The Physics of Rubber Elasticity*, Second Edition, Clarendon Press (1958). A summary of experimental results for several collagen-mucopolysaccharide composites is also presented in Table I.

TABLE I

| Material | Crosslinking | % MPS | $M_c$ ($\pm$ 10%) |
|---|---|---|---|
| Collagen | G (24, 7.4) | 0.0 | 1,500 |
| Collagen-H | G (24, 3.2) | 5.7 ± 1.2 | 9,400 |
| Collagen-H | G (48, 7.4) | 5.5 ± 1.3 | 1,200 |
| Collagen-H | G (24, 3.2 24, 7.4) | 4.0 ± 1.0 | 1,800 |
| Collagen-H | D (48, 90° C.) | 9.7 ± 1.0 | 2,800 |
| Collagen-CS-6 | G (24, 3.2) | 3.9 ± 3 | 6,800 |
| Collagen-CS-6 | D (48, 90° C.) | 9.6 ± 1.1 | 1,200 |
| Collagen-HA | G (24, 7.4) | 2.3 ± .4 | 2,200 |
| Collagen-HA | D (48, 90° C.) | 9.0 ± .5 | 2,500 |

G = Glutaraldehyde at 23° C. (hours, pH)
D = Dehydrothermal (hours, temp.)
H = Heparin
CS-6 = Chondroitin 6-sulfate
HA = Hyaluronic Acid

EXAMPLE 7

COMPOSITES FORMED BY COATING COLLAGEN WITH MUCOPOLYSACCHARIDES

Mucopolysaccharide solutions were prepared by dissolving 40 mg. of the mucopolysaccharide in 20 ml. citric acid-phosphate buffer (pH 3.2). A length of an insoluble collagen film was then added to the mucopolysaccharide solution and maintained at a constant temperature of 37° C. and allowed to incubate for about 24 hours. Glutaraldehyde was then added to the solution to give a resultant concentration of 0.025 M of aldehyde. The collagen was kept in this solution for another 24 hours and was subsequently transferred to a 0.025 M solution of glutaraldehyde maintained at a pH of 7.4. The latter step was done in order to insure efficient crosslinking of collagen. After 24 hours in the glutaraldehyde solution, the collagen fibers were rinsed three times with distilled water and transferred to a 0.2 weight percent solution of dimedone in order to remove excess, unreacted aldehydes. After another 24 hours in the dimedone solution, the fibers were rinsed five times with distilled water and kept in a citric acid-phosphate buffer solution at pH 7.4 at 4° C. The weight percent of mucopolysaccharide attached to the collagen was determined by hexosamine analysis. The molecular weight between crosslinks, $M_c$, was determined using the procedure described in Treloar, L. R. G., *The Physics of Rubber Elasticity*, 2nd ed., Clarendon Press (1958). The results are presented in Table II.

TABLE II

| Material | % MPS ($\pm$0.5) | $M_c$ ($\pm$500) |
|---|---|---|
| Collagen | 0 | 3800 |
| Collagen-CS-6 | 11.3 | 4100 |
| Collagen-CS-4 | 8.7 | 4000 |
| Collagen-HA | 8.2 | 4200 |

TABLE II-continued

| Material | % MPS ($\pm$0.5) | $M_c$ ($\pm$500) |
|---|---|---|
| Collagen-DS | 8.2 | 3900 |
| Collagen-H | 8.7 | 3800 |
| Collagen-KS | 10.5 | 3800 |

CS-6 = Chondroitin 6-sulfate
CS-4 = Chondroitin 4-sulfate
HA = Hyaluronic Acid
DS = Dermatan Sulfate
H = Heparin
KS = Keratan Sulfate

EXAMPLE 8

ENZYMATIC DEGRADATION OF COMPOSITES FORMED FROM COLLAGEN COATED WITH MUCOPOLYSACCHARIDE

A study of the enzymatic degradation of composites formed by coating a mucopolysaccharide onto collagen fibers as described in Example 7 was made. The mucopolysaccharide-coated collagen films, in the form of tape, were extended to a strain of 4.0±0.5% in the presence of a solution of collagenase (40 units/ml.) and the force induced on the tape was recorded as a function of time. The force was found to be representable by a single negative exponential of the time and hence a plot of the logarithmic force versus time yields a straight line. The slope of the straight line yields $1/\tau$—a value which is taken as a measure of the rate of enzymatic degradation of the collagen by the collagenase. The results are presented in Table III.

TABLE III

| Material | % MPS ($\pm$0.5) | $1/\tau \times 10^4$ ($\pm$0.07) (min$^{-1}$) |
|---|---|---|
| Collagen | 0 | 8.48 |
| Collagen-CS-6 | 11.3 | 1.46 |
| Collagen-CS-4 | 8.7 | 0.88 |
| Collagen-HA | 8.2 | 5.38 |
| Collagen-DS | 8.2 | 0.90 |
| Collagen-H | 8.7 | 0.98 |
| Collagen-KS | 10.5 | 1.10 |

EXAMPLE 9

ENZYMATIC DEGRADATION OF COMPOSITES FORMED FROM COPRECIPITATED COLLAGEN AND CHONDROITIN 6-SULFATE

Crosslinked composites of collagen and chondroitin 6-sulfate prepared according to the method of Example 4 were tested for their susceptibility to collagenase degradation. The technique used is described in the previous Example except that the strain imposed was 20±2%. The results are presented in Table IV.

TABLE IV

| % CS-6 ($\pm$0.2) | $M_c$ ($\pm$1000) | $1/\tau \times 10^2$ ($\pm$0.009) (min$^{-1}$) |
|---|---|---|
| 0 | 15000 | 0.255 |
| 1.8 | 14000 | 0.149 |
| 3.0 | 12000 | 0.153 |
| 4.8 | 13000 | 0.093 |
| 6.5 | 11000 | 0.084 |
| 8.6 | 9000 | 0.049 |
| 11.2 | 10000 | 0.052 |
| 13.3 | 12000 | 0.047 |
| 14.9 | 11000 | 0.064 |
| 16.0 | 14000 | 0.067 |

EXAMPLE 10

MECHANICAL PROPERTIES OF CROSSLINKED COLLAGEN-MUCOPOLYSACCHARIDE COMPOSITE MATERIALS

Mechanical testing was done on an Instron tester using a B-type load cell. Dumbell shaped specimens 0.25 in. wide and about 0.01 in. thick were prepared for each candidate material. The top end of the specimen was attached to the load cell of the Instron while the lower end was attached to the crosshead through a clamping device. The strain on the specimen was calculated based on the crosshead movement. All measurements were conducted at a constant elongation rate of 50%/minute in tension at 37° C. in a citric acid-phosphate buffer solution at pH 7.4.

Values of the force per unit area at rupture or ultimate tensile stress (U.T.S.), tangent to the stress-strain curve at 1% elongation (1% tangent modulus), elongation at break (E.B.), and work required to fracture (fracture work) were calculated for each material from the experimental stress-strain curve.

The results are presented in Table V below.

TABLE V

| Material | Crosslinking | % MPS | $M_c$ | 1% Tangent Modulus (psi) | U.T.S. (psi) | E.B. % | Fracture Work (psi-%) ± 10% |
|---|---|---|---|---|---|---|---|
| Thoracic Aorta | — | — | — | 50 | 360 | 85 | 21,000 |
| Collagen | D (24, 90° C.) | 0.0 | 9,200 | 235 ± 50 | 380 ± 10 | 40 ± 10 | 8,800 |
| Collagen | D (48, 90° C.) | 0.0 | 6,500 | 500 ± 65 | 525 ± 65 | 45 ± 5 | 10,800 |
| Collagen | G (0.25, 7.4) | 0.0 | 3,800 | 950 ± 100 | 334 ± 51 | 15 ± 2 | 5,000 |
| Collagen | G (24, 7.4) | 0.0 | 1,200 | 1800 ± 200 | 359 ± 11 | 10 ± 1 | 1,900 |
| Collagen-H | G (24, 3.2) | 5.7 ± 1.2 | 9,400 | 203 ± 30 | 130 ± 20 | 23 ± 2 | 1,200 |
| Collagen-H | G (48, 3.2) | 5.7 ± 1.2 | 6,800 | 475 ± 70 | 160 ± 20 | 16 ± 2 | 1,100 |
| Collagen-H | D (48, 90° C.) | 9.7 ± 1.0 | 2,800 | 300 ± 10 | 430 ± 40 | 35 ± 1 | 5,300 |
| Collagen-H | G (24, 7.4) | 5.5 ± 1.2 | 1,800 | 1900 ± 600 | 380 ± 50 | 14 ± 3 | 3,200 |
| Collagen-CS-6 | G (24, 3.2) | 3.9 ± 0.3 | 6,800 | 343 ± 120 | 130 ± 10 | 21 ± 2 | 1,100 |
| Collagen-CS-6 | G (48, 3.2) | 3.7 ± 0.3 | 5,500 | 226 ± 10 | 92 ± 40 | 16 ± 2 | 820 |
| Collagen-CS-6 | G (24, 7.4) | 3.5 ± 0.3 | 2,500 | 253 ± 92 | 133 ± 30 | 11 ± 3 | 650 |
| Collagen-CS-6 | D (48, 90° C.) | 9.6 ∓ 1.1 | 1,200 | 700 ± 65 | 631 ± 28 | 20 ± 1 | 7,100 |
| Collagen-HA | D (48, 90° C.) | 9.0 ± 0.5 | 2,500 | 430 ± 40 | 490 ± 70 | 20 ± 1 | 3,800 |

G = Glutaraldehyde at 23° C. (hours, pH)
H = Heparin
HA = Hyaluronic Acid
D = Dehydrothermal (hours, temp.)
CS-6 = Chondroitin 6-Sulfate

EXAMPLE 11

INCREASED TOUGHNESS DUE TO INCORPORATION OF MUCOPOLYSACCHARIDES

Comparison of specimens of collagen and crosslinked collagen-mucopolysaccharide composites at similar crosslinking levels suggests that the presence of the mucopolysaccharide significantly increases toughness of collagen. For example, the fracture work at similar levels of crosslinking from materials taken from the preceeding Table are presented in Table VI below.

TABLE VI

| Material | % MPS | $M_c$ | Fracture Work (psi-%) ± 10% |
|---|---|---|---|
| Collagen | 0.0 | 1200 | 1900 |
| Collagen-CS-6 | 9.6 ± 1.1 | 1200 | 7100 |

As can be seen, at constant crosslink density, the incorporation of about 10 weight percent chondroitin 6-sulfate in collagen increases the fracture work from about 1900 to about 7100 psi-%.

EXAMPLE 12

IN VITRO BLOOD-COMPATIBILITY OF COMPOSITES PREPARED USING DIFFERENT CROSSLINKING METHODS

The WBCT test provides an in vitro method for qualitatively evaluating the effects of materials on (1) blood coagulation, (2) platelet aggregation, and (3) red blood cell aggregation. This test is based upon the fact that blood isolated in a venous segment, lined by normal endothelium, shows signs of clotting within an hour, and within two to eight hours completely coagulates into a solid gel. Even normal endothelium cannot prolong the coagulation time of blood indefinitely when it is deprived of the protective effects of flow and natural filtration mechanisms. Thus, candidate non-thrombogenic materials can be considered to duplicate the effect of normal endothelium if, when in contact with blood, they do not cause clotting in less than 60 minutes. Blood so tested, however, must have a finite clotting time since prolongation of the clotting time of blood longer than 60 minutes raises the suspicion of artifactual delays such as protein adsorption or denaturation and is not conclusive in determining the surface effects of factor XII activation. If either denaturation of one or more of the protein factors of the coagulation process or some other form of anticoagulation (e.g., inhibition of a coagulation factor) is involved in whole blood clotting time (WBCT) prolongation, blood placed in contact with the test surface for 60 minutes normally will not clot even when transferred to an active surface such as glass. If, however, transferred blood does clot when WBCT prolongation must be due primarily to the surface and not to protein adsorption, denaturation, or permanent anticoagulation. In summary then, the WBCT test is used to qualitatively evaluate the effect of candidate materials on (1) blood coagulation, (2) platelet aggregation, and (3) red blood cell aggregation. Blood in contact with the candidate materials with WBCTs greater than one hour is transferred to glass and analyzed for heparin or heparin-like anticoagulants to clearly demonstrate that protein adsorption, denaturation, or permanent anticoagulation is not involved in prolongation of the clotting time. For further details of the WBCT test, See Lee, R. I., and White, P. D., *Am. J. Med. Sci.*, 145, 495 (1913), the teachings of which are hereby incorporated by reference.

Specifically, tubes of each test material, 4 cm. long and 0.7 cm. in diameter, were clamped at the bottom with a hemostat. One to two ml. of freshly drawn human blood was poured into each tube. To obtain a control clotting time, blood was also poured into glass tubes having similar dimensions as the test tubes. Each tube was placed on a heating block at 37° C. and was tilted every 30 seconds to observe the fluidity of the blood. The clotting time end point was arbitrarily taken to be the time at which the blood was totally transformed into gel.

The thrombin time (TT) test was used to detect low levels of the anticoagulant heparin in blood. Heparin is known to interfere with the catalysis, by thrombin, of the polymerization of fibrinogen to fibrin. When thrombin is added to citrated plasma, the conversion of fibrinogen to fibrin is inhibited in the presence of heparin. Generally, this test is performed by exposing plasma to the test surface in the presence of bovine thrombin under standardized conditions until coagulation is detected with a fibrometer. Plasma unexposed to a test surface is used as a control. For a more detailed description, see Biggs, R. and MacFarlane, R. G., *Human Blood Coagulation and Its Disorders*, Oxford (1962), the teachings of which are hereby incorporated by reference.

Specifically, thrombin time tests were carried out by placing blood in tubes of each test material for 60 minutes at 37° C. and anticoagulating the blood with 10% (V/V) of 3.8% (W/V) sodium citrate. The plasma was then separated from the cellular components by centrifugation at 23° C., and then kept on ice until the plasma was tested.

Control plasma (0.1 ml.), unexposed to a test surface, was coagulated with 0.1 ml. of bovine thrombin (Parke-Davis, Detroit, Mich.). The bovine thrombin activity was adjusted by dilution with normal saline, until the coagulation time was 20 seconds as measured with a fibrometer (Baltimore Biological Lab., Baltimore, Md.). Plasma previously exposed to each test surface, was coagulated in the same manner as the adjusted control (20 second thrombin time). Adjusted bovine activities ranging between 0.7 and 3.5 units per ml. were used in different phases of these tests. When heparin was present in blood exposed to a test surface, the thrombin time was found to be greater than 20 seconds. The exact heparin concentration in the exposed plasma was found by protamine sulfate neutralization. See Hardisty, R. M. and Ingrim, G. I. C., in *Bleeding Disorders*, Blackwell Scientific Publications, Oxford (1965). One mg. of protamine sulfate neutralizes the activity of about 85 units of heparin.

Protamine sulfate was added in varying amounts to the exposed plasma until the thrombin time was again 20 seconds. The level of protamine sulfate required to neutralize the activity of heparin quantitatively identifies the level of solubilized heparin in the sample. Once the number of units of heparin in each sample was known, the concentration of heparin in units per ml. in each whole blood sample was calculated by dividing the number of units by the sample volume and multiplying by 0.65, the volume fraction of plasma in whole blood. The thrombin time test only reveals defects in the mechanism for converting fibrinogen to fibrin. Selective adsorption of a plasma protein could in fact prevent whole blood from clotting when exposed to a surface. By transferring blood exposed to a test surface to an active surface such as glass, any coagulation defects caused by protein adsorption or anticoagulation became apparent if the blood failed to clot.

The results are presented in Table VII below.

TABLE VII

| Material | Crosslinking | % MPS | Control (min) | WBCT (min) | Washing | Thrombin Time (secs) | Eluted Heparin (units/ml) |
|---|---|---|---|---|---|---|---|
| Collagen | G (24, 7.4) | 0.0 | 3.5 | 25.3 ± 5 | | | |
| Collagen | G (24, 7.4) | 4.1 ± 1.0 | 3.0 | 60+ | | | |
| Collagen-H | G (24, 3.2) | 5.7 ± 1.2 | 3.5 | 60+ | $H_2O$ | 180+ | 2.75 |
| | | | | | Saline | 180+ | 0.33 |
| Collagen-H | G (48, 7.4) | 5.5 ± 1.3 | 3.5 | 60+ | | | |
| Collagen-H | D (48, 90° C.) | 9.7 ± 1.0 | 4.5 | 60+ | $H_2O$ | 180+ | 5.5 |
| | | | | | Saline | 180+ | 0.33 |
| Collagen-CS-6 | G (24, 3.2) | 3.9 ± 0.3 | 3.5 ± 0.5 | 23 ± 3 | | | |
| Collagen-CS-6 | D (48, 90° C.) | 9.7 ± 1.0 | 3.0 ± 0.5 | 60+ | | 20 | |
| Collagen-HA | G (24, 7.4) | 2.3 ± 0.4 | 3.5 ± 0.5 | 14 ± 0.5 | | | |

TABLE VII-continued

| Material | Crosslinking | % MPS | Control (min) | WBCT (min) | Washing | Thrombin Time (secs) | Eluted Heparin (units/ml) |
|---|---|---|---|---|---|---|---|
| Collagen-HA | D (48, 90° C.) | 9.0 ± 0.5 | 3.0 ± 0.5 | 21.5 ± 2.0 | | | |

G = Glutaraldehyde at 23° C. (hours, pH)
MPS = Mucopolysaccharide
D = Dehydrothermal (hours, temp.)
Control = Clotting time on glass
H = Heparin
H$_2$O = Washing for 3 days at 23° C. in water
CS-6 = Chondroitin 6-sulfate
Saline = Washing for 2 days in water followed by 3 days in normal saline at 37° C.
HA = Hyaluronic Acid

EXAMPLE 13

IN VITRO BLOOD-COMPATIBILITY OF COMPOSITES PREPARED FROM DIFFERENT MUCOPOLYSACCHARIDES

Collagen was extracted from rat tail tendon with 0.05 M acetic acid following the method of Piez, K. A. et al., J. Biochim. Biophys. Acta, 53, 596 (1961). A stock solution was stored under refrigeration at 4° C.

Chondroitin 6-sulfate from shark cartilage was purchased from Calbiochem, San Diego, CA. Hyaluronic acid from rooster comb was prepared according to method of Swann, D. A., Biochim. Biophys. Acta, 156, 17 (1968).

Films of crosslinked ionic collagen-mucopolysaccharide complexes were prepared as follows. A solution or dispersion of collagen was mixed with a solution of one each of the mucopolysaccharides at pH 3.2 with stirring. The resulting precipitate, a collagen-mucopolysaccharide ionic complex, was collected as a film-like residue which was air dried and immersed in a 0.02 M solution of glutaraldehyde, pH 7.4, over 48 hours at 23° C. Unreacted aldehydes were removed by reacting with a solution of dimedone.

Standardized in vitro hematological tests were carried out using freshly drawn human venous blood. Whole blood clotting time (WBCT) and thrombin time (TT) were determined as described in the previous Example.

The activated partial thromboplastin time (APTT) was determined by incubating citrated plasma with kaolin and cephalin (Thrombofax, Ortho, Raritan, N.J.), a partial thromboplastin, in tubes made from the test material and observing coagulation time with a fibrometer after recalcifying; a control consisted of repeating the procedure in the absence of the test surface. This test is described in more detail in Proctor, R. R. and Rapaport, S. I., Am. J. Clin. Path., 36, 212 (1961), the teachings of which are hereby incorporated by reference.

The prothrombin time (PT) was determined as the clotting time following recalcification of plasma containing a tissue extract thromboplastin (Hyland, Costa Mesa, CA) and previously placed in contact with the test material. This test is described in more detail in Thomson, J. M., A Practical Guide to Blood Coagulation and Haemostasis, Churchill, London (1970), the teachings of which are hereby incorporated by reference.

Platelet aggregation was studied by stirring the test material (in powder form) in platelet-rich plasma inside an aggregometer (Chrono-Log, Broomall, PA) and recording the optical density of the system as a function of time. Platelet aggregation was accompanied by an increase in transparency (decrease in optical density) of the originally turbid medium.

The result of all but the platelet aggregation test are presented in Table VIII below.

TABLE VIII

| Material | % MPS | WBCT (min.) | APTT (sec.) | TT (sec.) | PT (sec.) |
|---|---|---|---|---|---|
| Control | — | 3.5 ± 5 | 36.0 ± 0.5 | 19.5 ± 0.5 | 13.0 ± 0.2 |
| Collagen | — | 25 ± 5 | 57 ± 3 | 20.5 ± 0.5 | 25 ± 4 |
| Collagen-CS-6 | 9.6 ± 1.1 | >60 | 35.8 ± 0.4 | 21.0 ± 0.5 | 13.0 ± 0.2 |
| Collagen-HA | 9.0 ± 0.5 | 21.5 ± 2 | 36.6 ± 0.5 | 19.4 ± 0.4 | 13.2 ± 0.5 |
| Collagen-H | 9.7 ± 1.0 | >60 | >180 | >180 | 13.0 ± 0.3 |

In the platelet aggregation test, the optical density of collagen had dropped from an initial value of about 9 to a value of below 4 after 4 minutes whereas that of all of the composites containing mucopolysaccharides had only slightly dropped to a value of around 8.75 in the same time.

EXAMPLE 14

IN VIVO BLOOD COMPATIBILITY TESTING OF COMPOSITES

Crosslinked collage-mucopolysaccharide materials were sutured with little or no inconvenience. Little or no tearing was observed during suturing and no leakage was observed when tubular prostheses fabricated from collagen-chondroitin 6-sulfate were implanted as arterial grafts in sheep and dogs. Post surgical arterial flow observation using an ultrasonic signal detector showed that the collagen-chondroitin 6-sulfate tubular prosthesis grafted to the carotid artery of a lamb was capable of sustaining substantial steady arterial flow. This observation was repeated with the same results two weeks later just before removing the graft. Upon removal, the proximal lumen of the graft was found to be partially narrowed by the presence of thrombus; about 50% of the lumen was clear at that site. The distal end contained very little thrombus, while about 90% of the lumen was free and available for flow at that site. Thrombus appeared to initiate at the proximal suture line and extend to about 50% of the prosthetic length. When the graft was cut open longitudinally along its axis, the existing thrombus separated readily from the surface of the graft and did not appear to be attached to it. Initial observations made with the optical microscope indicated that neither large platelet clumps nor fibrinogen were attached to the implant lumenal surface. Microscopic observations also showed that a dense layer of granulation tissue was deposited on the exterior surface of the implant.

EXAMPLE 15

IN VIVO TESTING OF RESORPTION RESISTANCE OF AND ABSENCE OF FOREIGN BODY REACTION TOWARDS COMPOSITES

In this Example, crosslinked collagen-mucopolysaccharide membranes, prepared both by coating collagen with each of the mucopolysaccharides as described in Example 7 as well as by coprecipitating collagen with each of the mucopolysaccharides as described in Examples 2 and 3, were implanted subcutaneously in guinea pigs as described below.

The collagen-mucopolysaccharide membranes had been sterilized by the process used to crosslink them. Immersion in an aldehyde bath (and, in particular, in a glutaraldehyde bath) over several hours as described in Example 4, is well-known as an effective means of chemical sterilization of a variety of materials prior to implantation or other surgical procedures. It is also known that exposure to temperatures in excess of 100° C. over several hours is an alternative method of sterilization of materials that will be implanted or otherwise used in surgery. In addition, however, if the materials have been prepared considerably prior to grafting, it is preferable to disinfect them just before grafting by immersion in 70/30 isopropanol/water for 24 hours at 23° C. Immersion in the latter medium does not alter either the crosslink density or other important structural features of collagen-mucopolysaccharide composites. This medium can also be used for storage, over an indefinite period of time, of prostheses fabricated from the materials described in this application.

Subcutaneous implantation was carried out under aseptic conditions. White, Hartley, female guinea pigs, weighing approximately 400 grams were used as subjects. For 7 days prior to implantation, a weight-change history was recorded for each animal. Shortly before implantation, the back of each animal was sheared with electric clippers over an area of ca. 6 cm×5 cm and loose hair clippings were carefully removed with vacuum suction. The animal was then anesthesized by exposure to a mixture of oxygen and halothane, and its back was washed with 70/30 isopropanol/water.

A one-inch incision was made on one side of the back of the animal. The incision was made such that a pocket between the dermis and the panniculus carnosus was created. The specimen was inserted into this pocket such that the whole specimen lay flat within the pocket. The incision was then sutured with nylon sutures. A total of about 5 to 6 stitches were made to close the incision. The procedure was repeated with the other side of the guinea pig back, using an identical specimen. The right side was subsequently used for histological studies while specimens from the left side were, after explantation, used for physicochemical characterization.

On the 4th, 10th, and 20th postimplantation days, the animals were sacrificed by placing them in a desiccator containing ether. From both the left and right implantation sites, $1\frac{1}{2}'' \times 1\frac{1}{2}''$ squares of the tissues were cut below the subcutaneous layer such that the implanted specimens remained in the tissue. The tissue from the right side was placed in a 10% formalin solution and was subsequently used for histological studies as described below. The tissue from the left side was immersed in sterile Dulbecco's solution (50 ml) containing a few drops of chloroform (which acts as a bactericide) and stored under refrigeration for not more than 24 hours before the sample within it was removed.

Removal of the sample within the tissue was done by placing the tissue on the stage of a low powered microscope (equipped with a camera) and stripping the subcutaneous tissue from the dermis in such a way that the state of the sample within the tissue could be examined clearly with the microscope. This could be achieved by first cutting between the dermis and the subcutaneous tissue and gently separating the two parts by means of forceps. When viewed on the microscope, the state of the tissue and the sample embedded within it could be examined to reveal such features as the attachment of tissues to the implanted material. Removal of the sample from the tissue was done on the microscope stage by means of a forceps. After the materials had been removed from the tissue they were stored in Dulbecco's solution at 4° C. until required to determine the following physicochemical properties:

1. The fractional weight change of the sample $\Delta W/W_i$. This was obtained by determining the dry weight of the samples (after dehydration at 105° C. at a pressure of $10^{-3}$ mm. Hg. for 48 hours). The fractional weight change was then calculated as $$\Delta W/W_i = \frac{W_e - W_i}{W_i}$$

where $W_e$=dry weight of the explanted sample, and $W_i$=dry weight of the sample prior to implantation (the latter was determined by use of a control).

2. Tensile modulus, E, (in dynes/cm$^2$). This was obtained by the method described in Example 10 except that the modulus was determined as the slope of the straight portion of the stress-strain curve.

3. Molecular weight between crosslinks, $M_c$. This was measured as described in Example 4.

The characteristics of collagen-mucopolysaccharide specimens just before implantation as well as on the 4th, 10th and 20th days following implantation are presented in Table IX for materials that were prepared by coating collagen with various mucopolysaccharides prior to crosslinking and in Table X for materials prepared by coprecipitating collagen with mucopolysaccharides prior to crosslinking.

TABLE IX

COMPOSITES FORMED BY COATING COLIAGEN WITH MUCOPOLYSACCHARIDES.
PRE- AND POST-IMPLANTATION PROPERTIES

| Properties | Preimplantation | In vivo residence time | | |
| --- | --- | --- | --- | --- |
| | | 4 days | 10 days | 20 days |
| (1) Collagen | | | | |
| $\Delta W/W_i$ | 0.00 ± 0.04 | −0.16 ± 0.04 | −0.15 ± 0.04 | −0.31 ± 0.04 |

TABLE IX-continued
COMPOSITES FORMED BY COATING COLIAGEN WITH MUCOPOLYSACCHARIDES. PRE- AND POST-IMPLANTATION PROPERTIES

| Properties | Preimplantation | In vivo residence time | | |
| --- | --- | --- | --- | --- |
| | | 4 days | 10 days | 20 days |
| $E \times 10^{-9}$ (dynes cm$^{-2}$) | $3.3 \pm 0.3$ | $2.5 \pm 0.3$ | $1.4 \pm 0.3$ | $1.6 \pm 0.3$ |
| $M_c \times 10^{-3}$ | $3.8 \pm 0.5$ | $6.6 \pm 0.5$ | $6.1 \pm 0.5$ | $8.6 \pm 0.5$ |
| (2) Collagen-Hyaluronic Acid | | | | |
| $\Delta W/W_i$ | $0.00 \pm 0.04$ | $-0.12 \pm 0.04$ | $-0.30 \pm 0.04$ | $-0.28 \pm 0.04$ |
| $E \times 10^{-9}$ (dynes cm$^{-2}$) | $3.5 \pm 0.3$ | $2.3 \pm 0.3$ | $1.8 \pm 0.3$ | $-0.9 \pm 0.3$ |
| $M_c \times 10^{-3}$ | $4.2 \pm 0.5$ | $7.2 \pm 0.5$ | $6.7 \pm 0.5$ | $8.5 \pm 0.5$ |
| (3) Collagen - Heparan Sulfate | | | | |
| $\Delta W/W_i$ | $0.00 \pm 0.04$ | $-0.06 \pm 0.04$ | $+0.04 \pm 0.04$ | $+0.38 \pm 0.04$ |
| $E \times 10^{-9}$ (dynes cm$^{-2}$) | $4.0 \pm 0.3$ | $3.5 \pm 0.3$ | $3.8 \pm 0.5$ | $3.6 \pm 0.5$ |
| $M_c \times 10^{-3}$ | $3.8 \pm 0.5$ | $4.6 \pm 0.5$ | $4.7 \pm 0.5$ | $4.5 \pm 0.5$ |
| (4) Collagen - Heparin | | | | |
| $\Delta W/W_i$ | $0.00 \pm 0.04$ | $-0.02 \pm 0.04$ | $+0.08 \pm 0.04$ | $+0.32 \pm 0.04$ |
| $E \times 10^{-9}$ (dynes cm$^{-2}$) | $4.2 \pm 0.3$ | $3.9 \pm 0.3$ | $4.2 \pm 0.3$ | $4.3 \pm 0.3$ |
| $M_c \times 10^{-3}$ | $3.8 \pm 0.5$ | $4.3 \pm 0.5$ | $4.3 \pm 0.5$ | $3.6 \pm 0.5$ |
| (5) Collagen - Dermatan Sulfate | | | | |
| $\Delta W/W_i$ | $0.00 \pm 0.04$ | $-0.09 \pm 0.04$ | $-0.05 \pm 0.04$ | $+0.31 \pm 0.04$ |
| $E \times 10^{-9}$ (dynes cm$^{-2}$) | $3.9 \pm 0.3$ | $4.0 \pm 0.3$ | $3.0 \pm 0.3$ | $3.1 \pm 0.3$ |
| $M_c \times 10^{-3}$ | $4.0 \pm 0.5$ | $4.9 \pm 0.5$ | $5.3 \pm 0.5$ | $5.2 \pm 0.5$ |
| (6) Collagen-Chondroitin 6-sulfate | | | | |
| $\Delta W/W_i$ | $0.00 \pm 0.04$ | $-0.02 \pm 0.04$ | $-0.07 \pm 0.04$ | $+0.40 \pm 0.04$ |
| $E \times 10^{-9}$ (dynes cm$^{-2}$) | $4.0 \pm 0.3$ | $3.6 \pm 0.3$ | $3.2 \pm 0.3$ | $3.3 \pm 0.3$ |
| $M_c \times 10^{-3}$ | $4.1 \pm 0.5$ | $4.3 \pm 0.5$ | $5.7 \pm 0.5$ | $5.4 \pm 0.5$ |

TABLE X
COMPOSITES FORMED BY COPRECIPITATING COLLAGEN WITH CHONDROITIN 6-SULFATE; PRE- AND POST-IMPLANTATION PROPERTIES

| Properties | Preimplantation | In vivo residence time | | |
| --- | --- | --- | --- | --- |
| | | 4 days | 10 days | 20 days |
| (1) Collagen | | | | |
| $\Delta W/W_i$ | $0.00 \pm 0.02$ | $-0.16 \pm 0.02$ | $-0.52 \pm 0.02$ | $-0.60 \pm 0.02$ |
| $E \times 10^{-8}$ (dynes cm$^{-2}$) | $1.8 \pm 0.2$ | $1.3 \pm 0.2$ | $1.4 \pm 0.2$ | $0.7 \pm 0.2$ |
| $M_c \times 10^{-4}$ | $1.5 \pm 0.1$ | $2.4 \pm 0.1$ | $3.5 \pm 0.1$ | $3.8 \pm 0.1$ |
| (2) 1.8 wt-% Chondroitin 6-sulfate | | | | |
| $\Delta W/W_i$ | $0.00 \pm 0.02$ | $-0.20 \pm 0.02$ | $-0.28 \pm 0.02$ | $-0.39 \pm 0.2$ |
| $E \times 10^{-8}$ (dynes cm$^{-2}$) | $1.9 \pm 0.2$ | $1.5 \pm 0.2$ | $1.0 \pm 0.2$ | $1.0 \pm 0.2$ |
| $M_c \times 10^{-4}$ | $1.4 \pm 0.1$ | $1.8 \pm 0.2$ | $2.9 \pm 0.2$ | $3.0 \pm 0.2$ |
| (3) 4.8 wt-% Chondroitin 6-sulfate | | | | |
| $\Delta W/W_i$ | $0.00 \pm 0.02$ | $-0.04 \pm 0.02$ | $-0.08 \pm 0.2$ | $+0.33 \pm 0.2$ |
| $E \times 10^{-8}$ (dynes cm$^{-2}$) | $1.8 \pm 0.2$ | $1.5 \pm 0.2$ | $1.2 \pm 0.2$ | $1.3 \pm 0.2$ |
| $M_c \times 10^{-4}$ | $1.3 \pm 0.1$ | $1.5 \pm 0.2$ | $2.0 \pm 0.2$ | $2.4 \pm 0.2$ |
| (4) 11.2 wt-% Chondroitin 6-sulfate | | | | |
| $\Delta W/W_i$ | $0.00 \pm 0.02$ | $-0.04 \pm 0.02$ | $+0.18 \pm 0.2$ | $+0.65 \pm 0.2$ |
| $E \times 10^{-8}$ (dynes cm$^{-2}$) | $1.9 \pm 0.2$ | $1.6 \pm 0.2$ | $1.6 \pm 0.2$ | $1.7 \pm 0.2$ |
| $M_c \times 10^{-4}$ | $1.0 \pm 0.1$ | $1.4 \pm 0.1$ | $1.3 \pm 0.1$ | $1.6 \pm 0.1$ |

It is clear from Tables IV and X that, in almost all cases where collagen was crosslinked with a mucopolysaccharide, either after being coated or coprecipitated with a mucopolysaccharide, the fractional weight loss was significantly reduced indicating that the degradation of collagen had been effectively delayed by reaction with the mucopolysaccharide. The only exceptions were collagen coated with hyaluronic acid (a nonsulfated mucopolysaccharide). In most other cases, an occasional very small initial weight loss, possibly due to deswelling of the implanted specimen, was reversed usually by the 10th day until, by the 20th day, the implant was heavier than when implanted. The increase in weight of the implant was found to be due to adherence of some of the surrounding tissue onto the implant as the latter was removed from the animal. The tissue adhering on the implant was analyzed and found to be constituted almost entirely of collagen, an observation showing that new collagen had been synthesized on the implant by cells in the surrounding tissues. Thus, not only did reaction with the sulfated mucopolysaccharides significantly delay degradation of collagen but also yielded a composite material capable of eliciting synthesis of new connective tissue on its surface by cells in the surrounding tissue.

The protection from resorption afforded to collagen by reaction with sulfated mucopolysaccharides is also evident in the prevention of the substantial decrease in modulus E and decrease in crosslink density (increase in $M_c$) which is observed with collagen itself or with a collagen-hyaluronic acid composite. The maintenance of E and $M_c$ to relatively steady levels (within the experimental uncertainty) up to 20 days of implantation for composites of collagen and one each of the sulfated mucopolysaccharides is indicative of a crosslinked macromolecular network which remains largely intact for at least 20 days in the tissue of the living animal.

Histological studies were performed on the tissue/implant block removed from the right side of the animal on the 4th, 10th and 20th days. The standardized procedure used in preparing the specimens for histological examination was the following:

1. The tissue was fixed in 10% formalin (Fischer Scientific Co., N.J.) for at least 24 hours at room temperature.
2. It was then dehydrated by sequential immersion in water-ethyl alcohol mixtures containing 50%, 70%, 85%, 95% and 100% alcohol, the time of immersion being 1 hour per mixture.
3. The tissue was then immersed in dioxane for 2 hours before it was embedded in a tissue-embedding medium (Paraplast, Mpt. 56°–57° C.; Curtin Scientific Co., Houston, Tex.). Embedding was achieved by first placing the tissue in the molten paraffin kept at 58° C. for 4 hours, with hourly exchanges for the paraffin. Finally, the tissue was placed in a mould and embedded with a fresh supply of paraffin.
4. The paraffin block containing the tissue was then cooled to 0° C. in a bath containing chipped ice for 20 minutes and was then mounted on a microtome (Minot Custom Microtome; International Equipment Co., Needham Heights, Mass.). Slices of the paraffin containing the tissue were microtomed to thicknesses of about 6μ.
5. The microtomed specimen was then mounted on a clear microscope slide and deparaffinization was achieved by immersing the mounted specimen in two exchanges of xylene for 3 minutes each.
6. The specimen was then rehydrated by sequential immersion in water-ethyl alcohol mixtures containing 100%, 95%, 85%, 70%, 50% and 0% alcohol, the time of immersion being 1 hour per mixture. The specimen was finally rinsed thoroughly with distilled water.
7. The specimen was then stained with hematoxylin for 5 minutes and rinsed briefly with distilled water. Excess stain was removed by rinsing the specimen with 0.5% acid alcohol (70% ethyl alcohol in concentrated hydrochloric acid). The acid alcohol was finally removed by rinsing the specimen and immersing it in water for ½ hour.
8. The specimen was then stained with 0.5% aqueous eosin for 3 minutes and then rinsed with 5 exchanges of water.
9. The specimen was dehydrated as in (2) above and then rinsed a few times with xylene.
10. It was then mounted on a clean cover slip with a permanent mounting medium (Harleco Synthetic Resin; Hartman-Leddon Co., Philadelphia, Pa.).
11. The cover slip containing the stained specimen was examined with a microscope.

The histological studies revealed that the extent and severity of chronic inflammation in the tissue surrounding the collagen implant decreased steadily as the content of chondroitin 6-sulfate, in a series of implants based on coprecipitated collagen-chondroitin 6-sulfate composites, increased in the range 1.8 to 11.2 weight percent. These results showed that while the collagen used in the composite materials provoked, when used by itself, a moderate immune response, reaction of the collagen with chondroitin 6-sulfate led to practically complete suppression of this immune response. These findings were also made when the implant was based on composite materials prepared by coating collagen with one of the sulfated mucopolysaccharides. In summary, the histological observations showed that the ability of implanted collagen to provoke a foreign body reaction from the animal host could be controlled and suppressed by reaction with one each of the sulfated mucopolysaccharides.

EXAMPLE 16

STUDY OF THE EFFECT OF CHONDROITIN 6-SULFATE ON QUATERNARY STRUCTURE FORMATION OF COLLAGEN

Tendon collagen was extracted from tails of female rats in the age group 53–56 days. Unskinned tails were obtained in frozen form from Pel-Freez Animals, Rogers, Ark., and were stored at −10° C. for less than 5 days before use. Tendon fibers were removed using the procedure described by Dumitru and Garrett. See Dumitru, E. T. and Garrett, R. R., Arch. Biochem. Biophys., 66, 245 (1957). Collagen was extracted from fibers with 0.05 M acetic acid using a procedure which is based on those of Peiz et al. and Michaeli et al. See Piez, K. A., Lewis, M. S., Martin, G. P., and Gross, J., Biochim. Biophys. Acta, 53, 596 (1961); Michaeli, D., Annual Report NIH-NO1-HV-4-2984-1, National Technical Information Service, Springfield, Va., (1975); and Michaeli, D., Annual Report No. NIH-NO1-HV-4-2984-2, National Technical Information Service, Springfield, Va. (1976). Following extraction in 0.05 M acetic acid at 10° C., the resulting dispersion was centrifuged at 40,000 g over 1 hour. The pellet was discarded and NaCl was added to the supernatant to a concentration of 5%. The resulting precipitate was centrifuged and the supernatant was discarded while the pellet was redissolved in 0.05 M acetic acid. The cycle precipitation-centrifugation-redissolution was repeated twice more. The resulting solution of collagen in 0.05 M acetic acid was dialyzed against 0.02 M $HaH_2PO_4$ over 48 hours and was then centrifuged at 2,000 g over 10 minutes. The supernatant was discarded while the pellet was lyophilized and stored.

The final solution had an intrinsic viscosity in the range 11.0±0.3 dl/g in 0.05 M acetic acid at 26° C. The empirical index of native collagen content, determined with a 20-micron-thick film cast from solution, using the infrared spectroscopic procedure, was in the range of 1.42±0.04. The collagen particles were dispersed considerably, and their diffusion coefficient increased from 0.015 to 0.20 $cm^2$/second, as the solvent medium was changed from 0.05 M acetic acid to 0.5 M acetic acid. It was apparent that this preparation contained primarily "multimers" of the collagen molecule. An amino acid analysis using a Beckman Automatic Amino Acid Analyzer, Model 119B was made and compared favorably with composition data from rat tail tendon collagen preparations reported in the literature.

Chondroitin 6-sulfate was purchased from Sigma Chemical Co. (Type C from shark cartilage) and was used without further purification. The intrinsic viscosity was found to be 0.97 dl/g.

A series of experiments were run to study, by transmission electron microscopy, collagen fibrogenesis in the presence of chondroitin 6-sulfate.

Four basic types of procedures were followed. All solutions were kept at 4° C. For each procedure, the acid-soluble rat tail collagen in 0.05 M acetic acid at pH 3.5 was used. In procedure 1, this collagen solution was dialyzed versus saline solution, pH 6.0, and the addition of chondroitin 6-sulfate was omitted entirely. In procedure 2, chondroitin 6-sulfate solution, pH 6.5, was added to the collagen solution followed by dialysis versus saline, pH 6.0. In procedure 3, the collagen solution was dialyzed versus saline, pH 6.0, followed by the addition of chondroitin 6-sulfate solution, pH 6.0. In procedure 4, chondroitin 6-sulfate solution, pH 3.5 was added followed by dialysis versus saline solution, pH 6.0.

Electron photomicrographs of collagen fibrils prepared from each procedure were obtained by transmission electron microscopy. By use of a Pasteur pipette, the dispersion was dropped on a carbon-coated polymer-reinforced 75-mesh copper grid (Ernest F. Fullam, Inc., Schenectady, N.Y.). Excess dispersion was removed by gently applying filter paper to the edge of the grid. The sample was stained with an aqueous solution of 0.5% (w/v) phosphotungstinic acid (Ernest F. Fullam, Inc., Schenectady, N.Y.) for several seconds. The stain was quickly removed with filter paper as described above and the specimen was viewed in the microscope, which was a JEOLCO 100C transmission electron microscope at magnifications of $10,000\times$–$125,000\times$.

Procedure 1 produced collagen fibrils which displayed native banding. A relatively large amount of microfibrillar matter surrounded the banded fibril. Procedure 2, where chondroitin 6-sulfate solution was added until the ratio of chondroitin 6-sulfate/collagen in the dispersion was 50/50 w/w, produced fibrils characterized by banding known as fibrous long spacing (FLS).

In procedure 3, the amount of chondroitin 6-sulfate added, expressed as a ratio of chondroitin 6-sulfate added/collage w/w was 20/80. The resulting fibrils contained a mixture of FLS and segment long spacing (SLS) fibrils. In addition, the presence of microfibillar matter in the background was noted.

Procedure 4 gave fibrous precipitates with little or no banding of any kind. The detailed structure of precipitated fibrils was found to range with the amount of chondroitin 6-sulfate added to the collagen solution. It was found that a progressive loss in distinctiveness of fibrillar diameter occurred as the added chondroitin 6-sulfate/collagen ratio increased from 1/99 to 10/90 to 20/80. No axial periodic banding was observed in the photographs of fibrils obtained. This type of collagen may be referred to as noncrystalline collagen.

EXAMPLE 17
STUDY OF THE EFFECT OF CHONDROITIN 6-SULFATE ADDITION ON PLATELET ACTIVATION BY COLLAGEN

The four procedures described in Example 17 were used to prepare collagen fibrils for study of platelet aggregating activity.

Platelet aggregation studies were made by stirring human platelet rich plasma with the test material (in finely dispersed form) in an aggregometer (Chrono-Log, Broomall, Pa.). The light transmission was recorded over several minutes following rapid mixing of the test dispersion with the plasma.

The serotonin release factor of platelets was measured as follows. To every 40 ml of citrated freshly drawn whole human blood was added 0.3 ml of $C^{14}$-labelled serotonin. The blood was centrifuged for 20 min at 200 g to allow for settling of red and white cells. Platelet-rich plasma (PRP) was pipetted from the plastic centrifuge tube being a siliconized glass pipette. After the PRP had been exposed to the test surface, the platelets were removed by centrifugation. Centrifuged platelet-free plasma was tested for radioactivity labelled serotonin using a scintillation counter (Nuclear, Chicago). The release factor (R.F.) was computed from the following expression: R.F.$=(\#S-\#PPP)/(\#PRP-\#PPP)$, where $\#S=$number of counts of test sample, $\#PPP$ and $\#PRP=$number of counts for platelet-poor and platelet-rich plasma, respectively.

The results were as follows. Collagen fibrils with native banding, prepared according to Procedure 1, initiated significant platelet aggregation within 3–4 minutes. The dispersion of fibrils with hybrid SLS/FLS banding, prepared according to Procedure 3, gave a somewhat slower and weaker platelet reaction. Preliminary results indicated that the dispersion of FLS fibrils, prepared according to Procedure 2, showed some platelet aggregating activity, although this result is tentative.

Addition of increasing amounts of chondroitin 6-sulfate to the collagen solution, pH 3.5, prior to dialysis against saline in Procedure 4 gradually delayed and eventually abolished, the collagen-platelet reaction. Addition of only 1% w/w chondroitin 6-sulfate had no apparent effect on the rate or extent of platelet aggregation. Increase of the relative proportion of chondroitin 6-sulfate to 5% w/w delayed, however, significantly the aggregation reaction. Inhibition of the collagen-platelet reaction was very marked when 10% w/w chondroitin 6-sulfate was added to the collagen dispersion, and the inhibition was complete at 20% w/w chondroitin 6-sulfate.

Serotonin release from platelets was also gradually abolished as the amount of chondroitin 6-sulfate added to the collage dispersion following Procedure 4 was increased. Interpolation of results indicated that addition of 15–20% w/w chondroitin 6-sulfate reduced serotonin release below the level of detection with this assay.

In addition, two control experiments were performed. In the first, platelet rich plasma (PRP) was incubated with chondroitin 6-sulfate, and the collagen dispersion was subsequently added rapidly to PRP. The collagen-platelet reaction was delayed by about 3–4 minutes but eventually occurred with the same intensity, measured as asymptotic increase in light transmission, as the control. In the second control experiment, a collagen dispersion was rapidly added to PRP and, 15 seconds later, a chondroitin 6-sulfate solution was added rapidly. In this case, the collagen-platelet reaction was delayed by about 1 minute and subsequently occurred to the same extent as with the collagen control. In both cases, the concentration of collagen and of chondroitin 6-sulfate in PRP was the same, 16 μg/ml.

Those skilled in the art will know, or be able to ascertain by no more than routine experimentation, many equivalents to the specific embodiments expressly described herein. These are within the scope of this invention and are intended to be covered by the appended claims.

What is claimed is:

1. A process for preparing a crosslinked collagen-mucopolysaccharide composite material, comprising:
   a. soaking collagen in an aqueous acidic solution having a pH of below about 6;
   b. contacting said aqueous acidic solution of collagen with a mucopolysaccharide to produce a collagen-mucopolysaccharide product; and,
   c. covalently crosslinking said collagen-mucopolysaccharide product to an $M_C$ value of between about 800 and about 60,000.

2. A process of claim 1 wherein said covalent crosslinking is achieved by removing sufficient water to crosslink said collagen-mucopolysaccharide product to the desired $M_c$ value.

3. A process of claim 1 wherein said covalent crosslinking is achieved by employing a chemical crosslinking agent.

4. A process of claim 3 wherein said chemical crosslinking agent comprises an aldehyde.

5. A process of claims 1, 2, or 3 wherein said mucopolysaccharide is selected from hyaluronic acid, chondroitin 6-sulfate, chondroitin 4-sulfate, heparin, heparan sulfate, keratan sulfate or dermatan sulfate.

6. A process of claim 5 wherein said collagen and mucopolysaccharide are contacted in the presence of acetic acid.

7. A process of claim 1 wherein said collagen comprises collagen fibrils and said collagen fibrils are soaked for a sufficient time in an aqueous solution having a pH sufficiently low to remove substantially all banding from said fibrils thereby producing noncrystalline collagen fibrils.

8. A process of claim 1 wherein steps a and b are carried out at a pH of about 3.

9. A process of claim 1 wherein said collagen-mucopolysaccharide product is covalently crosslinked to an $M_c$ value of between about 5,000 and about 10,000.

10. A process of claim 9 wherein said mucopolysaccharide is selected from the group consisting of hyaluronic acid, chondroitin 6-sulfate, chondroitin 4-sulfate, heparin, heparan sulfate, keratan sulfate or dermatan sulfate.

11. A process of claims 1 or 10 wherein said mucopolysaccharide is present in an amount sufficient to provide between about 6 percent and about 15 percent, by weight, of said mucopolysaccharide in said collagen-mucopolysaccharide product.

* * * * *